(12) United States Patent
Schaub et al.

(10) Patent No.: US 11,453,645 B2
(45) Date of Patent: Sep. 27, 2022

(54) PROCESS FOR PRODUCING SUBSTITUTED AMINO ALCOHOLS

(71) Applicant: BASF SE, Ludwigshafen am Rhein (DE)

(72) Inventors: Thomas Schaub, Ludwigshafen (DE); Martin Ernst, Ludwigshafen (DE); Pilar Calleja, Heidelberg (DE); A. Stephen K. Hashmi, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/291,390

(22) PCT Filed: Oct. 29, 2019

(86) PCT No.: PCT/EP2019/079474
§ 371 (c)(1),
(2) Date: May 5, 2021

(87) PCT Pub. No.: WO2020/094454
PCT Pub. Date: May 14, 2020

(65) Prior Publication Data
US 2022/0002247 A1    Jan. 6, 2022

(30) Foreign Application Priority Data
Nov. 9, 2018    (EP) ..................................... 18205448

(51) Int. Cl.
*C07D 211/58* (2006.01)
*C07C 213/02* (2006.01)
*C07C 231/12* (2006.01)
*C07C 253/30* (2006.01)

(52) U.S. Cl.
CPC .......... *C07D 211/58* (2013.01); *C07C 213/02* (2013.01); *C07C 231/12* (2013.01); *C07C 253/30* (2013.01)

(58) Field of Classification Search
CPC .................................................. C07D 211/58
USPC ...................................................... 546/244
See application file for complete search history.

(56) References Cited

U.S. PATENT DOCUMENTS

| 5,359,082 | A | 10/1994 | Koehler et al. |
| 5,741,955 | A | 4/1998 | Beatty |
| 6,639,114 | B2 | 10/2003 | Ahlers et al. |

FOREIGN PATENT DOCUMENTS

| EP | 0 562 345 | 9/1993 |
| EP | 1 352 894 | 10/2003 |
| WO | WO-2009/129097 A1 | 10/2009 |

OTHER PUBLICATIONS

Calleja, Chemistry—A European Journal (2019), 25(40), 9498-9503.*
Ye, Nature Communications | (2018) 9:410.*
Molnar, ChemCatChem (2017), 9(22), 4175-4178.*
Balaraman, J. Am. Chem. Soc. 2010, 132, 16756-16758.*
Calleja, Chem. Eur. J. 2019, 25, 9498-9503.*
Dysona, Catal. Sci. Technol., 2016, 6, 3302.*
"1-isocyanocyclohex-1-ene", Selected Organic Reactions Database (SORD), Oct. 4, 2012, 1978, pp. 1-5.
"Bulletin de la Societe chimique France", 1969, pp. 126-127.
Becke, et al., "Eine neue Darstellungsweise von a-N-Formylaminonitrilen, a-NFormylaminosaureamiden und a-sowie P-Aminosauren", Liebigs Annalen der Chemie, vol. 735, 1970, pp. 27-34.
Boltjes, et al., "Gd-TEMDO: Design, Synthesis, and MRI Application", Chemistry—A European Journal, vol. 22, Issue 22, Mar. 15, 2016, pp. 7352-7356.
European Search Report for EP Patent Application No. 18205448.6, dated Apr. 26, 2019, 4 pages.
International Search Report for PCT Patent Application No. PCT/EP2019/079474, dated Jan. 21, 2020, 4 pages.
Kothandaraman, et al., "Efficient Reversible Hydrogen Carrier System Based on Amine Reforming of Methanol", Journal of the American Chemical Society, vol. 139, Issue 7, Feb. 2, 2017, pp. 2549-2552.
Meier, et al., "The synthetic potential of the isocyanide-cyanide rearrangement", Chemische Berichte, vol. 120, Issue 1, 1987, pp. 1-4.
Rezayee, et al., "Iron-Catalyzed Hydrogenation of Amides to Alcohols and Amines", ACS Catalysis, vol. 6, Issue 10, Aug. 29, 2016, pp. 6377-6383.

(Continued)

*Primary Examiner* — Nizal S Chandrakumar
(74) *Attorney, Agent, or Firm* — Grüneberg and Myers PLLC

(57) ABSTRACT

A process for producing a compound of the formula (I)

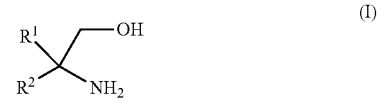

involves at least reacting a compound of the formula (II)

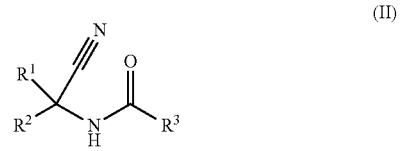

with hydrogen and water in the presence of at least one homogeneous transition metal catalyst TMC 1.

8 Claims, No Drawings

(56) References Cited

OTHER PUBLICATIONS

Sheldon B. Markofsky, "Nitro Compounds, Aliphatic", Ullmann's Encyclopedia of Industrial Chemistry, Oct. 15, 2011, pp. 291-300.
Wang, et al., "Versatile Synthesis of Free and N-Benzyloxycarbonyl-Protected 2,2-Disubstituted Taurines", in European Journal of Organic Chemistry, vol. 2008, Issue 2, Dec. 18, 2007, pp. 350-355.
Xie, et al., "Catalytic hydrogenation of aromatic and aliphatic nitriles in organic/aqueous biphasic system", Catalysis Communications, vol. 5, Issue 5, May 2004, pp. 237-238.
Xie, et al., "Catalytic hydrogenation of benzonitrile and alkyl nitrile in aqueous/organic biphase system", Chinese Journal of Catalysis, vol. 25, Issue 8, 2004, pp. 611-614.
International Search Report dated Jan. 21, 2020 in PCT/EP2019/07474.
Written Opinion dated Jan. 21, 2020 in PCT/EP2019/07474.
Calleja, et al., "Ruthenium-Catalyzed Deaminative Hydrogenation of Amino Nitriles: Direct Access to 1,2-Amino Alcohols," Chem. Eur. J. 10.1002/chem.201900531, 8 pages.
Kanemitsu, et al., "Catalytic Asymmetric Synthesis of (R)-(--)-Calycotomine, (S)-(--)-Salsolidine and (S)-(--)-Carnegine," SYNLETT 2006, No. 10, pp. 1595-1597.
Molnár, et al., "Ruthenium-Catalyzed Deaminative Hydrogenation of Aliphatic and Aromatic Nitriles to Primary Alcohols," ChemCatChem 2017, 9, 4175-4178.

\* cited by examiner

PROCESS FOR PRODUCING SUBSTITUTED AMINO ALCOHOLS

CROSS-REFERENCE TO RELATED APPLICATIONS

This application is the National Stage entry under § 371 of International Application No. PCT/EP2019/079474, filed on Oct. 29, 2019, and which claims the benefit of priority to European Application No. 18205448.6, filed on Nov. 9, 2018. The content of each of these applications is hereby incorporated by reference in its entirety.

BACKGROUND OF THE INVENTION

Field of the Invention

The present invention relates to a process for producing a compound of the formula (I)

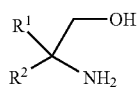

(I)

comprising at least the process step:

a) reacting a compound of the formula (II)

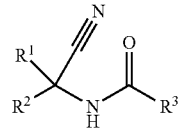

(II)

with hydrogen and water in the presence of at least one homogeneous transition metal catalyst TMC 1.

Description of Related Art

Compound of the formula (I), also called substituted amino alcohols according to formula (I) hereinafter, are valuable compounds, which are produced industrially. For example, 2-amino-2-methyl-1-propanol is a useful organic base for neutralizing and solubilizing applications, used in toiletries and cosmetics, used in conjunction with fatty acids as a dispersing agent, employed as formaldehyde scavenge and as a wetting agent as described in: Nitro Compounds, Aliphatic, Ullmann's Encyclopedia of Industrial Chemistry, DOI: 10.1002/14356007.a17_401.pub2.

Currently, substituted amino alcohols according to formula (I) are produced technically by the nitration of alkanes, followed by a Henry reaction with formaldehyde and then reduction to the amino alcohol, as exemplified for 2-amino-2-methyl-1-propanol in Nitro Compounds, Aliphatic, Ullmann's Encyclopedia of Industrial Chemistry, DOI: 10.1002/14356007.a17_401.pub2. and in WO2009/129097 A1:

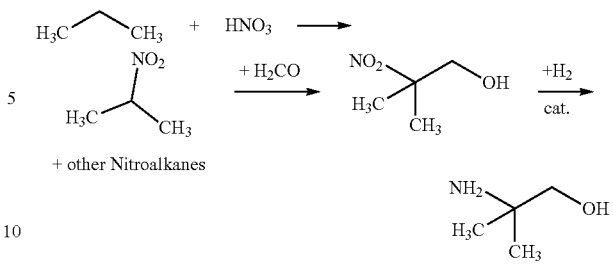

This protocol has some severe drawbacks: First of all the nitration of the alkane is not very selective and several other nitroalkanes are formed as by-products like nitromethane, nitroethane or 1-nitropropane, which have to be separated and are reducing the yield regarding the used propane as described in Nitro Compounds, Aliphatic, Ullmann's Encyclopedia of Industrial Chemistry, DOI: 10.1002/14356007.a17_401.pub2. Also, this approach fails for the synthesis of more complex amino alcohols according to formula (I) due to the low selectivity in the nitration of the alkane. Another major disadvantage are issues in the nitration/work-up as many nitroalkanes are shock-sensitive and can explode when not treated properly.

The reductive hydrolysis of nitriles using transition metal catalysts is described for aliphatic as well as araliphatic nitriles by using ruthenium- or nickel catalysts whereby the nitrile is hydrogenated in the presence of water and ammonia is formed as a by-product:

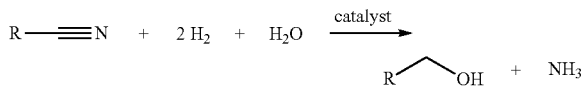

This transition metal catalyzed reductive hydrolysis of the nitrile group is described for example in a) Catalysis Communications, 2004, 5, 237-238; b) Chinese Journal of Catalysis, 2004, 25, 611-614; c) Bulletin de la Societe chimique France, 1969, 1, 126-127; d) U.S. Pat. No. 5,741,955; e) ChemCatChem, 2017, 9, 4175-4178. But in none of these reports the synthesis of substituted amino alcohols according to formula (I) is described.

The application of the reductive nitrile hydrolysis for the synthesis of substituted amino alcohols according to formula (I) has the drawback, that the closest starting material, aminonitriles, are not stable under the conditions necessary for the reductive nitrile hydrolysis. At the elevated temperatures of 80-150° C. in the presence of water necessary for the reductive nitrile hydrolysis, the free aminonitriles are hydrolyzing in a reverse Strecker reaction and therefore the desired amino alcohols are not formed:

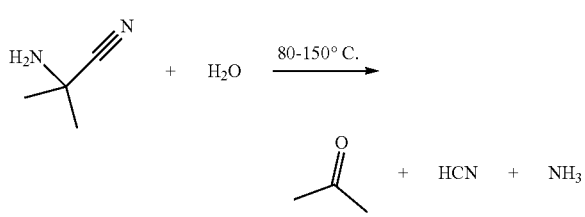

On the other hand, if the amino-function in the aminonitrile is protected as the HCl-salt, usually hydrolysis of the nitrile group to the amino-acid occurs as described in European Journal of Organic Chemistry, 2008, 350-355):

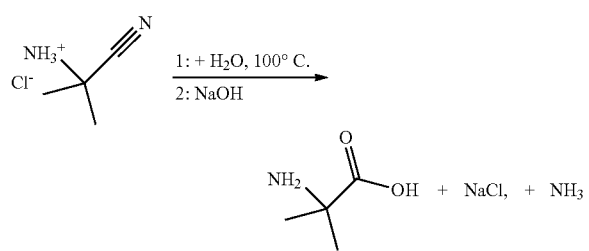

To overcome these issues, suitable protecting groups are necessary which also can be introduced as well as removed easily. For example, N-formyl-amines can be in principle deprotected via hydrogenation using homogeneous hydrogenation catalysts based on Iron or Ruthenium, whereby the free amine and methanol is formed as described for example in a) ACS Catalysis, 2016, 6, 6377-6383; b) Journal of the American Chemical Society, 2017, 139, 2549-2552). But this strategy was so far not applied to the synthesis of amino alcohols according to formula (I).

The protection of the amine-function as an amide can easily be achieved. For example, the corresponding N-formyl-α-aminonitriles are readily accessible by the reaction of a cyanohydrin with formamide in acetic acid as the solvent as described in Liebigs Annalen der Chemie, 1970, 735, 27-34:

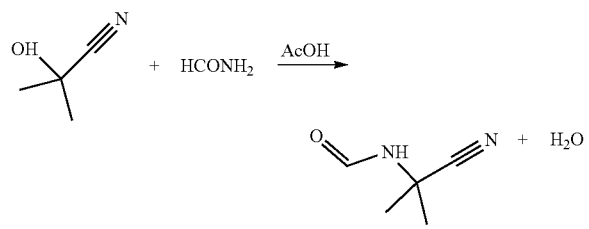

N-formyl-α-aminonitriles can also be synthesized by the reaction of an α-aminonitrile with a formate ester or a mixed formic/acetic-acid anhydride as described in a) Chemische Berichte, 1987, 120, 1-4; b) Chemistry—A European Journal, 2016, 22, 7352-7356; c) Sel. Org. React. Database (SORD), 1978, 20121004:

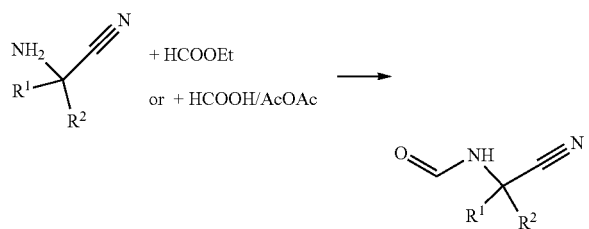

The hydrogenation of N-formyl-α-aminonitriles is described in EP 0562345 A2 using heterogeneous transition metal catalysts under anhydrous conditions but using this protocol no amino alcohols according to formula (I) were formed, instead substituted imidazoles are the main product due to a consecutive hydrogenation of the nitrile to an amine, followed by cyclisation.

SUMMARY OF THE INVENTION

Proceeding from this prior art, it is an object of the invention to provide a technical and economically advantageous process for the production of amino alcohols of formula (I).

This object is achieved by a process for producing a compound of the formula (I)

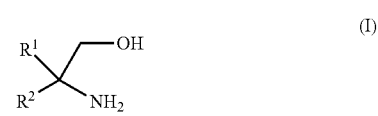

wherein
$R^1$ is hydrogen or an organic radical having from 1 to 40 carbon atoms,
$R^2$ is an organic radical having from 1 to 40 carbon atoms, or $R^1$ and $R^2$ together with the atoms connecting them, form a divalent organic group having from 1 to 40 carbon atoms, comprising at least the process step:
a) reacting a compound of the formula (II)

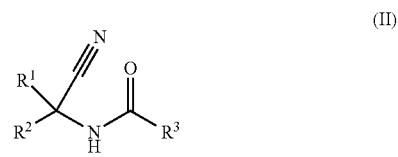

wherein $R^1$ and $R^2$ have the same meaning as in formula (I), and
$R^3$ is hydrogen or an organic radical having from 1 to 40 carbon atoms, with hydrogen and water in the presence of at least one homogeneous transition metal catalyst TMC 1.

DETAILED DESCRIPTION OF THE INVENTION

Surprisingly it was found, that when a compound of the formula (II), also referred to hereinafter as protected aminonitrile, in particular a formyl-protected aminonitrile is used under the conditions of the transition metal catalyzed reductive nitrile hydrolysis, the reaction proceeds in high selectivity and the amine can be deprotected using the same catalyst by hydrogenating the formyl-group to methanol. If other carboxylic acids are used for the amino protection, they are also reduced to the corresponding alcohol and removed (e.g. acetate to ethanol). Using this protocol, no salts are produced during the deprotection. Another advantage of this approach is the significantly broader substrate scope towards compounds of the formula (I), also called substituted amino alcohols of the formula (I) compared to the above described state-of-the-art nitro-route, as cyanohydrins—as well as the aminonitriles—are easily available from a broad range of ketones and aldehydes.

The substituents according to the present invention are, unless restricted further, defined as follows:

The term "organic radical having from 1 to 40 carbon atoms" as used in the present text refers to, for example, $C_1$-$C_{40}$-alkyl radicals, $C_1$-$C_{40}$-substituted alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, silyl radicals having from 3 to 24 carbon atoms, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C$—), methoxy ($H_3C$—O—) and hydroxymethyl (HOC($H_2$)—). Therefore, the term "organic radical having from 1 to 40 carbon atoms" comprises beside alkoxy radicals for example also dialkylamino radicals, monoalkylamino radicals or alkylthio radicals.

In the present description, the term radical is used interchangeably with the term group, when defining the variables $R^X$ in the presented formulas.

The term "alkyl" as used in the present text encompasses linear or singly or multiply branched saturated hydrocarbons which can also be cyclic. Preference is given to a $C_1$-$C_{18}$-alkyl radical such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having one or more C—C double bonds which can be cumulated or alternating.

The term "saturated heterocyclic radical" as used in the present text refers to, for example, monocyclic or polycyclic, substituted or unsubstituted aliphatic or partially unsaturated hydrocarbon radicals in which one or more carbon atoms, CH groups and/or $CH_2$ groups have been replaced by heteroatoms which are preferably selected from the group consisting of the elements O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl, isopropyl- and tert-butyl-substituted derivatives thereof.

The term "aryl" as used in the present text refers to, for example, aromatic and optionally fused polyaromatic hydrocarbon radicals which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-ditert-butylphenyl or 4-trifluoromethylphenyl.

The term "heteroaromatic radical" as used in the present text refers to, for example, aromatic hydrocarbon radicals in which one or more carbon atoms or CH groups have been replaced by nitrogen, phosphorus, oxygen or sulfur atoms or combinations thereof. These may, like the aryl radicals, optionally be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers to, for example, aryl-comprising substituents whose aryl radical is linked via an alkyl chain to the remainder of the molecule. Preferred examples are benzyl, substituted benzyl, phenethyl, substituted phenethyl and the like.

The terms fluoroalkyl and fluoroaryl mean that at least one hydrogen atom, preferably more than one and at most all hydrogen atoms, of the corresponding radical have been replaced by fluorine atoms. Examples of preferred fluorine-comprising radicals are trifluoromethyl, 2,2,2-trifluoroethyl, pentafluorophenyl, 4-trifluoromethylphenyl, 4-perfluoro-tert-butylphenyl and the like.

$R^1$ in formulas I and II is hydrogen or an organic radical having from 1 to 40 carbon atoms, preferably hydrogen, acyclic or cyclic, substituted or unsubstituted $C_1$-$C_{10}$-alkyl, substituted or unsubstituted $C_6$-$C_{10}$-aryl or substituted or unsubstituted $C_7$-$C_{12}$-arylalkyl, in particular hydrogen or methyl, in particular methyl.

$R^2$ in formulas I and II is an organic radical having from 1 to 40 carbon atoms, preferably acyclic or cyclic, substituted or unsubstituted $C_1$-$C_{10}$-alkyl, substituted or unsubstituted $C_6$-$C_{10}$-aryl or substituted or unsubstituted $C_7$-$C_{12}$-arylalkyl, in particular methyl.

Alternatively, $R^1$ and $R^2$ together with the atoms connecting them, form a divalent organic group having from 1 to 40 carbon atoms. Preferably, $R^1$ and $R^2$ form a divalent organic group selected from the group consisting of —$CH_2CH_2$—, —$CH_2CH_2CH_2$—, —$CH_2CH_2CH_2CH_2$—, —$CH_2CH_2CH_2CH_2CH_2$—, —$CH_2CH_2NHCH_2CH_2$— and —$CH_2CH_2OCH_2CH_2$—.

$R^3$ in formula (II) is hydrogen or an organic radical having from 1 to 40 carbon atoms, preferably hydrogen, acyclic or cyclic, substituted or unsubstituted $C_1$-$C_{10}$-alkyl, substituted or unsubstituted $C_6$-$C_{10}$-aryl or substituted or unsubstituted $C_7$-$C_{12}$-arylalkyl, in particular $R^3$ is hydrogen. In one embodiment of the present invention, the inventive process is characterized in that $R^3$ is hydrogen.

In the process of the invention, the compound of the formula (II) is reacted with hydrogen and water in the presence of at least one homogeneous transition metal catalyst TMC 1 (also called hydrogenation catalyst or simply transition metal catalyst TMC 1 hereinafter).

The homogeneous transition metal catalyst TMC 1 comprises a transition metal selected from metals of groups 7, 8, 9 or 10 of the periodic table of the elements according to IUPAC, such as Mn, Fe, Ru, Os, Co, Rh, Ir, Ni, Pd or Pt, preferably Ru.

In one embodiment of the present invention, the inventive process is characterized in that the homogeneous transition metal catalyst TMC 1 comprises a transition metal selected from the group consisting of metals of groups 7, 8, 9 and 10 of the periodic table of the elements according to IUPAC, such as Mn, Fe, Ru, Os, Co, Rh, Ir, Ni, Pd or Pt, preferably ruthenium, rhodium, iridium, nickel, platinum and palladium, in particular Ru.

In one embodiment of the present invention, the inventive process is characterized in that the transition metal of transition metal catalyst TMC 1 is Ru.

In one embodiment of the present invention, the inventive process is characterized in that the transition metal catalyst TMC 1 is a homogeneous catalyst, wherein the transition metal of the transition metal catalyst TMC 1 is Ru.

The hydrogenation catalyst of the process of the invention can be employed in the form of a preformed metal complex which comprises the metal compound and one or more ligands. Alternatively, the catalytic system is formed in situ in the reaction mixture by combining a metal compound, herein also termed pre-catalyst, with one or more suitable ligands to form a catalytically active metal complex in the reaction mixture.

Suitable pre-catalysts are selected from neutral metal complexes, oxides and salts of ruthenium. Ruthenium compounds that are useful as pre-catalyst are, for example, [Ru(p-cymene)Cl$_2$]2, [Ru(benzene)Cl$_2$]n, [Ru(CO)$_2$Cl$_2$]n, [Ru(CO)$_3$Cl$_2$]$_2$, [Ru(COD)(allyl)], [RuCl$_3$.H$_2$O], [Ru(acetylacetonate)$_3$], [Ru(DMSO)$_4$Cl$_2$], [Ru(PPh$_3$)$_3$Cl$_2$], [Ru(cyclopentadienyl)(PPh$_3$)$_2$Cl], [Ru(cyclopentadienyl)(CO)$_2$Cl], [Ru(cyclopentadienyl)(CO)$_2$H], [Ru(cyclopentadienyl)(CO)$_2$]2, [Ru(pentamethylcyclopentadienyl)(CO)$_2$Cl], [Ru(pentamethylcyclopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]2, Ruthenocen, [Ru(2,2'-bipyridin)$_2$(Cl)$_2$.H$_2$O], [Ru(COD)(Cl)$_2$H]$_2$, [Ru(pentamethylcyclopentadienyl)(COD)Cl], [Ru$_3$(CO)$_{12}$] and [Ru(tetraphenylhydroxycyclopentadienyl)(CO)$_2$H].

For the hydrogenation of the process according to the present invention any complex ligands known in the art, in particular those known to be useful in ruthenium catalysed hydrogenations may be employed.

Suitable ligands of the catalytic system for the hydrogenation of the process according to the invention are, for example, mono-, bi-, tri- and tetra dentate phosphines of the formulae IV and V shown below,

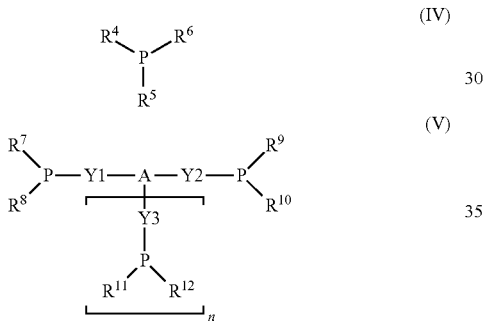

n is 0 or 1;
$R^4$ to $R^{12}$ are, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
  where the substituents are selected from the group consisting of: F, Cl, Br, OH, CN, NH$_2$ and $C_1$-$C_{10}$-alkyl;
A is
i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S,
  where the substituents are selected from the group consisting of: $C_1$-$C_4$-alkyl, phenyl, F, Cl, Br, OH, OR$^{16}$, NH$_2$, NHR$^{16}$ or N(R$^{16}$)$_2$
  where R$^{16}$ is selected from $C_1$-$C_{10}$-alkyl and $C_5$-$C_{10}$-aryl;
or ii) a bridging group of the formula (VI) or (VII):

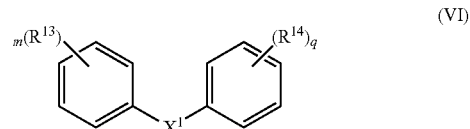

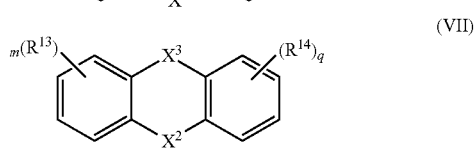

m, q are, independently of one another, 0, 1, 2, 3 or 4;
$R^{13}$, $R^{14}$ are, independently of one another, selected from the group $C_1$-$C_{10}$-alkyl, F, Cl, Br, OH, OR$^{15}$, NH$_2$, NHR$^{15}$ and N(R$^{15}$)$_2$
  where R$^{15}$ is selected from $C_1$-$C_{10}$-alkyl and $C_5$-$C_{10}$-aryl;
$X^1$, $X^2$ are, independently of one another, NH, O or S;
$X^3$ is a bond, NH, NR$^{16}$, O, S or CR$^{17}$R$^{18}$;
$R^{16}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
  where the substituents are selected from the group consisting of: F, Cl, Br, OH, CN, NH$_2$ and $C_1$-$C_{10}$-alkyl;
$R^{17}$, $R^{18}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S,
  where the substituents are selected from the group consisting of: F, Cl, Br, OH, CN, NH$_2$ and $C_1$-$C_{10}$-alkyl;
$Y^1$, $Y^2$, $Y^3$ are, independently of one another, a bond, unsubstituted or at least monosubstituted methylene, ethylene, trimethylene, tetramethylene, pentamethylene or hexamethylene,
  where the substituents are selected from the group consisting of: F, Cl, Br, OH, OR$^{15}$, CN, NH$_2$, NHR$^{15}$, N(R$^{15}$)$_2$ and $C_1$-$C_{10}$-alkyl,
  where R$^{15}$ is selected from $C_1$-$C_{10}$-alkyl and $C_5$-$C_{10}$-aryl.

A is a bridging group. For the case that A is selected from the group unsubstituted or at least monosubstituted $C_1$-$C_6$-alkane, $C_3$-$C_{10}$-cycloalkane, $C_3$-$C_{10}$-heterocycloalkane, $C_5$-$C_{14}$-aromatic and $C_5$-$C_6$-heteroaromatic for the case (n=0), two hydrogen atoms of the bridging group are replaced by bonds to the adjacent substituents $Y^1$ and $Y^2$. For the case (n=1), three hydrogen atoms of the bridging group are replaced by three bonds to the adjacent substituents $Y^1$, $Y^2$ and $Y^3$.

For the case that A is P (phosphorus), the phosphorus forms for the case (n=0) two bonds to the adjacent substituents $Y^1$ and $Y^2$ and one bond to a substituent selected from the group consisting of $C_1$-$C_4$-alkyl and phenyl. For the case (n=1), the phosphorus forms three bonds to the adjacent substituents $Y^1$, $Y^2$ and $Y^3$.

For the case that A is N (nitrogen), the nitrogen for the case (n=0) forms two bonds to the adjacent substituents $Y^1$ and $Y^2$ and one bond to a substituent selected from the group consisting of $C_1$-$C_4$-alkyl and phenyl. For the case (n=1), the nitrogen forms three bonds to the adjacent substituents $Y^1$, $Y^2$ and $Y^3$.

For the case that A is O (oxygen), n=0. The oxygen forms two bonds to the adjacent substituents $Y^1$ and $Y^2$.

Preference is given to complex catalysts which comprise at least one element selected from ruthenium and iridium.

In a preferred embodiment, the process according to the invention is carried out in the presence of at least one complex catalyst which comprises at least one element selected from the groups 8, 9 and 10 of the Periodic Table of the Elements and also at least one phosphorus donor ligand of the general formula (V), where n is 0 or 1;

$R^7$ to $R^{12}$ are, independently of one another, unsubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S;

A is
i) a bridging group selected from the group unsubstituted $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S;
or
ii) a bridging group of the formula (VI) or (VII):

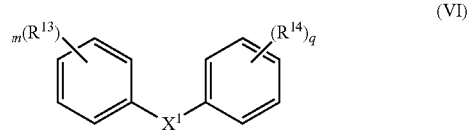

(VI)

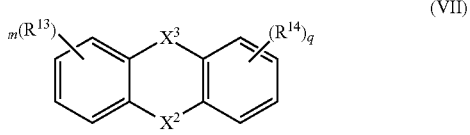

(VII)

m, q are, independently of one another, 0, 1, 2, 3 or 4;

$R^{13}$, $R^{14}$ are, independently of one another, selected from the group $C_1$-$C_{10}$-alkyl, F, Cl, Br, OH, $OR^{15}$, $NH_2$, $NHR^{15}$ and $N(R^{15})_2$,
where $R^{15}$ is selected from $C_1$-$C_{10}$-alkyl and $C_5$-$C_{10}$-aryl;

$X^1$, $X^2$ are, independently of one another, NH, O or S;

$X^3$ is a bond, NH, $NR^{16}$, O, S or $CR^{17}R^{18}$;

$R^{16}$ is unsubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S;

$R^{17}$, $R^{18}$ are, independently of one another, unsubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S;

$Y^1$, $Y^2$, $Y^3$ are, independently of one another, a bond, unsubstituted methylene, ethylene, trimethylene, tetramethylene, pentamethylene or hexamethylene.

In a further preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (VIII), where

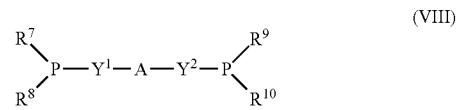

(VIII)

$R^7$ to $R^{10}$ are, independently of one another, unsubstituted or at least monosubstituted $C_1$-$C_{10}$-alkyl, $C_1$-$C_4$-alkyl-diphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;

A is
i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S,
where the substituents are selected from the group consisting of: $C_1$-$C_4$-alkyl, phenyl, F, Cl, Br, OH, $OR^{15}$, $NH_2$, $NHR^{15}$ or $N(R^{15})_2$
where $R^{15}$ is selected from $C_1$-$C_{10}$-alkyl and $C_5$-$C_{10}$-aryl;
or
ii) a bridging group of the formula (VI) or (VII):

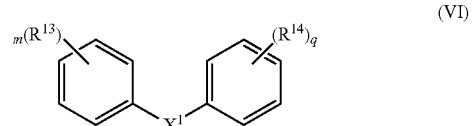

(VI)

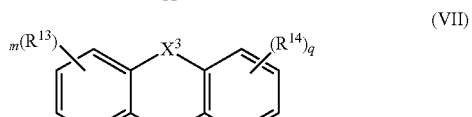

(VII)

m, q are, independently of one another, 0, 1, 2, 3 or 4;

$R^{13}$, $R^{14}$ are, independently of one another, selected from the group $C_1$-$C_{10}$-alkyl, F, Cl, Br, OH, $OR^{15}$, $NH_2$, $NHR^{15}$ and $N(R^{15})_2$,
where $R^{15}$ is selected from $C_1$-$C_{10}$-alkyl and $C_5$-$C_{10}$-aryl;

$X^1$, $X^2$ are, independently of one another, NH, O or S, $X^3$ is a bond, NH, $NR^{16}$, O, S or $CR^{17}R^{18}$;

$R^{16}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;

$R^{17}$, $R^{18}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

$Y^1$, $Y^2$ are, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^{15}$, CN, $NH_2$, $NHR^{15}$, $N(R^{15})_2$ and $C_1$-$C_{10}$-alkyl, where $R^{15}$ is selected from $C_1$-$C_{10}$-alkyl and $C_5$-$C_{10}$-aryl.

In a further preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (IX),

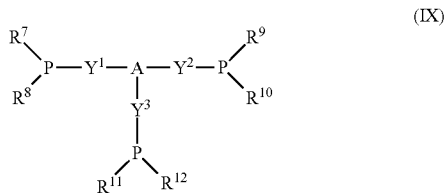

(IX)

where $R^7$ to $R^{12}$ are, independently of one another, unsubstituted or at least monosubstituted $C_1$-$C_{10}$-alkyl, $C_1$-$C_4$-alkyl-diphenylphosphine, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

A is a bridging group selected from the group unsubstituted or at least monosubstituted N, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S, where the substituents are selected from the group consisting of: $C_1$-$C_4$-alkyl, phenyl, F, Cl, Br, OH, $OR^{15}$, $NH_2$, $NHR^{15}$ or $N(R^{15})_2$ where $R^{15}$ is selected from $C_1$-$C_{10}$-alkyl and $C_5$-$C_{10}$-aryl;

$Y^1$, $Y^2$, $Y^3$ are, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^{15}$, CN, $NH_2$, $NHR^{15}$, $N(R^{15})_2$ and $C_1$-$C_{10}$-alkyl, where $R^{15}$ is selected from $C_1$-$C_{10}$-alkyl and $C_5$-$C_{10}$-aryl.

In a further preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (VIII), where $R^7$ to $R^{10}$ are, independently of one another, methyl, ethyl, isopropyl, tert-butyl, cyclopentyl, cyclohexyl, phenyl, or mesityl;

A is
i) a bridging group selected from the group methane, ethane, propane, butane, cyclohexane, benzene, napthalene and anthracene;
or
ii) a bridging group of the formula (X) or (XI):

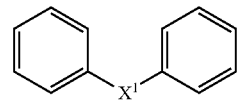

(X)

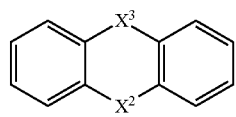

(XI)

$X^1$, $X^2$ are, independently of one another, NH, O or S;

$X^3$ is a bond, NH, O, S or $CR^{17}R^{18}$;

$R^{17}$, $R^{18}$ are, independently of one another, unsubstituted $C_1$-$C_{10}$-alkyl;

$Y^1$, $Y^2$ are, independently of one another, a bond, methylene or ethylene.

In a particularly preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (XII) or (XIII),

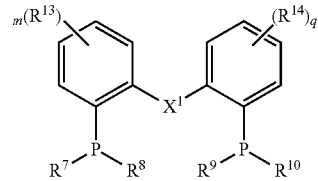

(XII)

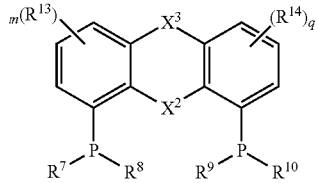

(XIII)

where for m, q, $R^7$, $R^8$, $R^9$, $R^{10}$, $R^{13}$, $R^{14}$, $X^1$, $X^2$ and $X^3$, the definitions and preferences listed above are applicable.

In an embodiment, the process according to the invention is carried out in the presence of at least transition metal one complex catalyst and monodentate ligands of the formula IV are preferred herein are those in which $R^{5a}$, $R^{5b}$ and $R^6$ are each phenyl or alkyl optionally carrying 1 or 2 $C_1$-$C_4$-alkyl substituents and those in which $R^7$, $R^8$ and $R^9$ are each $C_5$-$C_8$-cycloalkyl or $C_2$-$C_{10}$-alkyl, in particular linear unbranched n-$C_2$-$C_{10}$-alkyl. The groups $R^{5a}$ to $R^6$ may be different or identical. Preferably the groups $R^{5a}$ to $R^6$ are identical and are selected from the substituents mentioned herein, in particular from those indicated as preferred. Examples of preferable monodentate ligands IV are triphenylphosphine (TPP), Triethylphosphine, tri-n-butylphosphine, tri-n-octylphosphine and tricyclohexylphosphine.

In another embodiment, the process according to the invention is carried out in the presence of at least one transition metal complex catalyst and at least one phosphorus donor ligand selected from the group consisting of 1,2-bis(diphenylphosphino)ethane (dppe), 1,2-bis(diphenylphosphino)propane (dppp), 1,2-bis(diphenylphosphino) butane (dppb), 2,3-bis(dicyclohexylphosphino)ethane (dcpe), 4,5-bis(diphenylphosphino)-9,9-dimethylxanthene (xantphos), bis(2-diphenylphosphinoethyl)phenylphosphine and 1,1,1-tris(diphenylphosphinomethyl)ethane (triphos).

In a further particularly preferred embodiment, the process according to the invention is carried out in the presence of a complex catalyst which comprises ruthenium and at least one phosphorus donor ligand selected from the group 4,5-bis(diphenylphosphino)-9,9-dimethylxanthene (xantphos), bis(2-diphenylphosphinoethyl)phenylphosphine and 1,1,1-tris(diphenylphosphinomethyl)ethane (triphos).

In a further particularly preferred embodiment, the process according to the invention is carried out in the presence of a complex catalyst which comprises iridium and also at least one phosphorus donor ligand selected from the group 4,5-bis(diphenylphosphino)-9,9-dimethylxanthene (xantphos), bis(2-diphenylphosphinoethyl)phenylphosphine and 1,1,1-tris(diphenylphosphinomethyl)ethane (triphos).

Within the context of the present invention, $C_1$-$C_{10}$-alkyl is understood as meaning branched, unbranched, saturated and unsaturated groups. Preference is given to alkyl groups having 1 to 6 carbon atoms ($C_1$-$C_6$-alkyl). More preference is given to alkyl groups having 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted with one or more substituents selected from the group F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from N, O, S, oxo, $C_3$-$C_{10}$-cycloalkyl, phenyl, $C_5$-$C_{10}$-heteroaryl comprising at least one heteroatom selected from N, O, S, $C_5$-$C_{10}$-heterocyclyl comprising at least one heteroatom selected from N, O, S, naphthyl, amino, $C_1$-$C_{10}$-alkylamino, $C_5$-$C_{10}$-arylamino, $C_5$-$C_{10}$-heteroarylamino comprising at least one heteroatom selected from N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol or $C_1$-$C_{10}$-alkylsulfonyl.

The above definition for $C_1$-$C_{10}$-alkyl applies correspondingly to $C_1$-$C_{30}$-alkyl and to $C_1$-$C_6$-alkane.

$C_3$-$C_{10}$-cycloalkyl is understood in the present case as meaning saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted with one or more substituents as has been defined above in connection with the group $C_1$-$C_{10}$-alkyl.

The active hydrogenation catalyst can be generated in situ in the reaction mixture by adding the ligands to the above-mentioned precursors. The molar ratio between the transition metal and the ligand is in the range of 2:1 to 1:50, preferable in the range of 1:1 to 1:10 most preferably in the range of 1:2 to 1:5.

In addition to the one or more ligands selected from the groups of ligands described above the catalytic system of the inventive process may also include at least one further ligand which is selected from halides, amides, carboxylates, acetylacetonate, aryl- or alkylsufonates, hydride, CO, olefins, dienes, cycloolefins, nitriles, aromatics and heteroaromatics, ethers, $PF_3$, phospholes, phosphabenzenes, and mono-, di- and polydentate phosphinite, phosphonite, phosphoramidite and phosphite ligands. Preferably the catalyst also contains CO as a ligand.

The active catalyst can also be preformed in a dedicated synthetic step. Appropriate preformed catalysts can be [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(binap)(Cl)$_2$], [Ru(PMe$_3$)$_4$(H)$_2$], [Ru(PEt$_3$)$_4$(H)$_2$], [Ru(Pn-Pr$_3$)$_4$(H)$_2$], [Ru(Pn-Bu$_3$)$_4$(H)$_2$], [Ru(Pn-Octyl$_3$)$_4$(H)$_2$], [Ru(Pn-Bu$_3$)$_4$(H)$_2$], [Ru(PnOctyl$_3$)$_4$(H)$_2$], [Ru(PPh$_3$)$_3$(CO)(H)Cl] and [Ru(PPh$_3$)$_3$(CO)(H)$_2$], preferably [Ru(PPh$_3$)$_3$(CO)(H)Cl], [Ru(PPh$_3$)$_3$(CO)Cl$_2$], [Ru(PPh$_3$)$_3$(CO)(H)$_2$], and most preferably the active catalyst is [Ru(PPh$_3$)$_3$(CO)(H)Cl].

In one embodiment of the present invention, the inventive process is characterized in that the homogeneous transition metal catalyst TMC 1 is selected from the group consisting of [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(binap)(Cl)$_2$], [Ru(PMe$_3$)$_4$(H)$_2$], [Ru(PEt$_3$)$_4$(H)$_2$], [Ru(Pn-Pr$_3$)$_4$(H)$_2$], [Ru(Pn-Bu$_3$)$_4$(H)$_2$], [Ru(Pn-Octyl$_3$)$_4$(H)$_2$], [Ru(Pn-Bu$_3$)$_4$(H)$_2$], [Ru(PnOctyl$_3$)$_4$(H)$_2$], [Ru(PPh$_3$)$_3$(CO)(H)Cl] and [Ru(PPh$_3$)$_3$(CO)(H)$_2$], preferably [Ru(PPh$_3$)$_3$(CO)(H)Cl], [Ru(PPh$_3$)$_3$(CO)Cl$_2$], [Ru(PPh$_3$)$_3$(CO)(H)$_2$ and most preferably [Ru(PPh$_3$)$_3$(CO)(H)Cl].

If a preformed active catalyst is used, it can also be beneficial to add additional ligand of the formula IV or V to the reaction mixture.

In the inventive process the amount of transition metal catalyst TMC 1 used based on the amount of compound of formula (II), also called protected aminonitrile of formula (II), can be varied in a wide range. Usually the transition metal catalyst TMC 1 is used in a substoichiometric amount relative to the protected aminonitrile of formula (II). Typically, the amount of transition metal catalyst TMC 1 is not more than 50 mol %, frequently not more than 20 mol % and in particular not more than 10 mol % or not more than 5 mol %, based on the amount of protected aminonitrile of formula (II). An amount of transition metal catalyst TMC 1 of from 0.001 to 50 mol %, frequently from 0.001 mol % to 20 mol % and in particular from 0.005 to 5 mol %, based on the amount the protected aminonitrile of formula (II) is preferably used in the process of the invention. Preference is given to using an amount of transition metal catalyst TMC 1 of from 0.01 to 5 mol %. All amounts of transition metal complex catalyst TMC 1 indicated are calculated as transition metal and based on the amount of the compound of formula (II).

In one embodiment of the present invention, the inventive process is characterized in that the homogeneous transition metal catalyst TMC 1 is used in an amount of 0.001 mol % to 20 mol %, calculated as transition metal and based on the amount of the compound of the formula (II) used in the process.

The reaction of the compound of the formula (II) with hydrogen and water can principally be performed according to all processes known to a person skilled in the art which are suitable for the reaction of a protected aminonitrile with $H_2$ in the presence of water.

The hydrogen ($H_2$) used for the reduction reaction can be used in pure form or, if desired, also in the form of mixtures with other, preferably inert gases, such as nitrogen or argon. Preference is given to using $H_2$ in undiluted form.

The hydrogen can be applied discontinuously or continuously, e.g. by bubbling $H_2$ gas through the reaction mixture.

The reaction is typically carried at a $H_2$ pressure in the range from 0.1 to 400 bar, preferably in the range from 5 to 200 bar, more preferably in the range from 10 to 180 bar.

In one embodiment of the present invention, the inventive process is characterized in that the reaction between the compound of the formula (II), water and hydrogen is performed at a pressure in the range from 10 to 180 bar.

In one embodiment of the present invention, the inventive process is characterized in that the hydrogenation is carried out at different $H_2$ pressures. Preferably, first, at a lower $H_2$ pressure in the range from 1 to 80 bar, preferably in the range from 10 and 80 bar, the nitrile function is completely reductively hydrolyzed to the alcohol function. Afterwards the $H_2$ pressure is increased to a pressure in the range from 90 to 200 bar, preferably in the range from 100 to 180 bar to completely deprotect the amine group via hydrogenation of the amide group.

In case that inert salts are present from the synthesis of the starting material, the compounds of formula (I), like NaCl, $(NH_4)_2SO_4$ or $(NH_4)H_2PO_4$, the reductive nitrile hydrolysis is usually not affected by these salts.

The reaction can principally be performed continuously, semi-continuously or discontinuously. Preference is given to a continuous process.

The reaction can principally be performed in all reactors known to a person skilled in the art for this type of reaction and who will therefore select the reactors accordingly. Suitable reactors are described and reviewed in the relevant prior art, e.g. appropriate monographs and reference works such as mentioned in U.S. Pat. No. 6,639,114 B2, column 16, line 45-49. Preferably, for the reaction an autoclave is employed which may have an internal stirrer and an internal lining.

The inventive process can be performed in a wide temperature range. Preferably the reaction is performed at a temperature in the range from 20° C. to 200° C., more preferably in the range from 50° C. to 180° C., in particular in the range from 100° C. to 170° C.

In one embodiment of the present invention, the inventive process is characterized in that the process is performed at a temperature in the range from 50° C. to 180° C., preferably in the range from 100° C. to 170° C.

The reductive nitrile hydrolysis is carried out in the presence of water. The reaction can be run in water as the solvent but also in combination with a solvent. Use of water-solvent mixtures is preferred in the reductive nitrile hydrolysis. Suitable solvents are selected from aliphatic hydrocarbons, aromatic hydrocarbons, ethers or alcohols and mixtures thereof. Preferred solvents are aliphatic hydrocarbons such as pentane, hexane, heptane, octane or cyclohexane;

aromatic hydrocarbons such as benzene, toluene, xylenes, ethylbenzene, mesitylene or benzotrifluoride;

ethers such as dioxane, tetrahydrofuran, 2-methyl-tetrahydrofuran, diethyl ether, dibutyl ether, methyl t-butyl ether, diisopropyl ether, dimethoxyethane, or diethylene glycol dimethyl ether and other glymes (ethers of various oligomers and polymers of propyleneglycols and ethyleneglycols);

alcohols such as methanol, ethanol, 2-propanol, 1-butanol, iso-butanol, tert-butanol, pentanol, hexanol, ethylhexanol, octanol, methoxyethanol, ethyleneglycol, diethyleneglycol, triethyleneglycol and higher polyethyleneglycols.

Preference is given to using a solvent selected from the group of solvents consisting of ethers and alcohols, preferably consisting of dioxane, tetrahydrofuran, glymes, methanol and ethanol.

In one embodiment of the present invention, the inventive process is characterized in that the reaction between the compound of the formula (II), water and hydrogen is performed in the presence of a solvent selected from the group of solvents consisting of ethers and alcohols, preferably consisting of dioxane, tetrahydrofuran, glymes, methanol and ethanol.

If desired, mixtures of two or more of the afore-mentioned solvents can also be used.

The molar ratio of water to solvent when additional solvents are used is in the range between 50:1 to 1:50, preferably between 2:1 to 1:30, most preferably 2:1 to 1:10.

Alternatively, the process of the invention can be carried out in the absence of any of the above-mentioned organic solvents, so-called neat conditions, preferably in the presence of the compound of the formula (I) as solvent together with water.

The composition obtained in the reductive nitrile hydrolysis of the invention comprises the compound of the formula (I), an amino alcohol. The work-up of the reaction mixture of the inventive process and the isolation of the amino alcohol of formula (I) are carried out in a customary manner, for example by filtration, an extractive work-up or by a distillation, for example under reduced pressure. The compound of the formula (I) I may be obtained in sufficient purity by applying such measures or a combination thereof, obviating additional purification steps. Alternatively, further purification can be accomplished by methods commonly used in the art, such as chromatography or distillation.

In one embodiment of the present invention, the inventive process is characterized in that the compound of the formula (I) is separated from the transition metal catalyst after the reductive nitrile hydrolysis via distillation.

The distillation residue usually still comprises the transition metal catalyst in an active form, that can be reused in a new reductive nitrile hydrolysis step, that is a new process step a) or b). As long as the distillation conditions, in particular the temperature treatment, are not too harsh, the transition metal catalyst remains active. When high-boiling solvents are used, only the compounds of formula (I), (II) and (Ill) and water may be distilled off and the catalyst remains dissolved in the high-boiling solvent.

In one embodiment of the present invention, the inventive process is characterized in that the homogeneous transition metal catalyst TMC 1 is recycled by removing the compound of the formula (I) and other volatile compounds of the reaction mixture via distillation.

The composition obtained in the reductive nitrile hydrolysis of the present invention comprises the compound of the formula (I), which is a substituted amino alcohol. In case that no complete deprotection of the amino-function is achieved in the reductive nitrile hydrolysis, the composition can also contain a compound of formula (III), also called amine protected amino alcohol hereinafter.

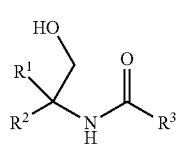

(III)

Further deprotection of the protected amino alcohol of formula (III) to the desired amino alcohol according to formula (I) can easily be achieved either by acidic hydrolysis or a further reductive deprotection of the amine.

In one embodiment of the present invention, the inventive process is characterized in that the nitrogen-carbon bond of the amide group —N(H)—C(=O)— of a compound of the formula (III), which is formed as an intermediate product in process step a),

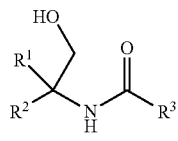

(III)

is cleaved in a second process step
b) by converting the amide group —NH—C(=O)—R³ into the amino group —NH₂ or its corresponding ammonium group —NH₃⁺ by hydrolysis, preferably by an acidic hydrolysis, or hydrogenation of the amide group —NH—C(=O)—R³ under formation of the amino group —NH₂ and the primary alcohol HO—CH₂—R³ via a hemiaminal —NH—CH(—OH)—R³ followed by further hydrogenation of the formed aldehyde HC(=O)—R³ to the primary alcohol HO—CH₂—R³.

The second process step can be done directly with the reaction mixture obtained in process step a) of the inventive process without previous isolation of the intermediate of the formula (III) from the desired product of the formula (I). Process step b) can also be performed after isolation of the compound of the formula (III) from the reaction mixture obtained in process step a) of the inventive process.

The conditions for the hydrolysis of an amide to the parent carboxylic acid and the corresponding amine are well known to a person skilled in the art. The hydrolysis of the amide group is usually done by using a strong acid (e.g. hydrochloric acid or sulfuric acid) or a strong base (e.g. sodium hydroxide), preferably in both cases in combination with heat.

Alternatively, the amide group of the compound of the formula (III) can be cleaved by hydrogenation, preferably by application of increased H₂ pressure or increased temperature compared with process step a) or by adding a second transition metal catalyst TMC 2, which is preferably more active than transition metal catalyst TMC 1.

Transition metal catalysts, which are suitable for the hydrogenation of the amide group —NH—C(=O)—R³ are known to a person skilled in the art. A very reactive transition metal catalyst TMC 2 for the hydrogenation of the amide group —NH—C(=O)—R³ is a transition metal catalyst, which comprises a transition metal M selected from metals of groups 7, 8, 9 and 10 of the periodic table of elements according to IUPAC, in particular Ru, and tridentatde ligands of formula XIV, XV or XVI.

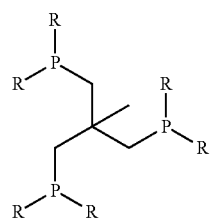

XIV

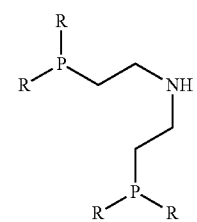

XV

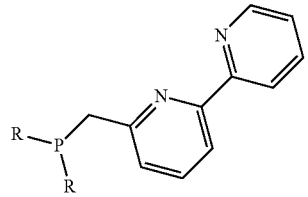

XVI

Preferably in process step b) the same transition metal catalyst is used as in process step a), but H₂ pressure and/or temperature are increased.

The protected aminonitrile according to the formula (II) as the starting material can be prepared in different ways, depending on R³ and the available precursors. R³ in formula (II) is hydrogen or an organic radical having from 1 to 40 carbon atoms, preferably hydrogen, acyclic or cyclic, substituted or unsubstituted $C_1$-$C_{10}$-alkyl, substituted or unsubstituted $C_6$-$C_{10}$-aryl or substituted or unsubstituted $C_7$-$C_{12}$-arylalkyl, in particular R³ is hydrogen.

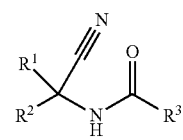

(II)

The synthesis of formyl protected aminonitrile (R³=H) of formula (II) can be achieved in different ways.

Starting from cyanohydrins, which are easily accessible by the reaction of the corresponding ketone or aldehyde with HCN, the protected aminonitrile of formula (II) is obtained by the reaction with formamide in acidic media like AcOH (see: Liebigs Annalen der Chemie, 1970, 735, 27-34):

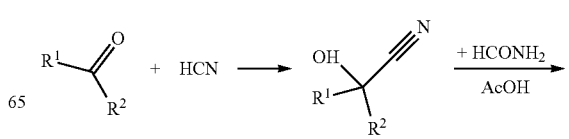

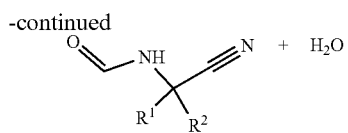

N-formyl-α-aminonitriles can also be synthesized by the reaction of an α-aminonitrile with a formate ester or a mixed formic/acetic-acid anhydride (see: a) Chemische Berichte, 1987, 120, 1-4; b) Chemistry—A European Journal, 2016, 22, 7352-7356; c) Sel. Org. React. Database (SORD), 1978, 20121004). The corresponding aminonitriles are easily accessible by the reaction of the corresponding cyanohydrin with $NH_3$ and/or $NH_4Cl$.

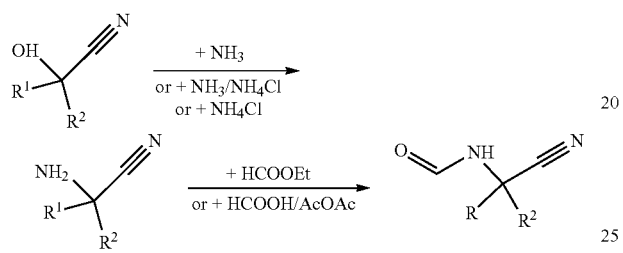

The synthesis of protected aminonitriles of formula (II) with other carboxylates as protecting groups like acetyl ($R^3$=$CH_3$) can be achieved in a similar way. For example, the acetyl protected amino nitrile of formula (I) can be prepared via the reaction of an aminonitrile with acetic acid anhydride or the acid chloride:

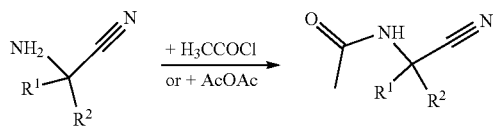

The invention is illustrated by the examples which follow, but these do not restrict the invention.

Figures in percent are each based on % by weight, unless explicitly stated otherwise.

General

All chemicals and solvents were purchased from Sigma-Aldrich or ABCR and used without further purification.

$^1H$ and $^{13}C$ NMR spectra were recorded on Bruker Avance 200 MHz spectrometer and were referenced to the residual proton ($^1H$) or carbon ($^{13}C$) resonance peaks of the solvent. Chemical shifts (δ) are reported in ppm.

1. Synthesis of the Protected Aminonitriles, the Compounds of the Formula (II)

1.1 Synthesis of N-(1-cyanocyclohexyl)formamide

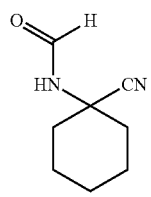 [SMILES: N#CC1(NC=O)CCCCC1]

A ca. 20 mL pressure tube (Ace tube) was charged with 1-hydroxycyclohexane-1-carbonitrile (1.252 g, 10.0 mmol), formamide (1.19 mL, 30 mmol), and acetic acid (0.57 mL, 10 mmol). The tube was then flushed with argon and closed. It was then placed into a 120° C. pre-heated oil bath and the mixture was stirred at this temperature for 4 h. The crude material was purified by flash chromatography ($SiO_2$, DCM/MeOH 1:0 to 50:1) to yield 1.439 g (95% yield) of desired product as an off-white solid (96% purity by GC analysis). $^1H$ NMR in $CDCl_3$-d show a 3.5:1 mixture of isomers. Major isomer: $^1H$ NMR (200 MHz, $CDCl_3$) δ 8.18 (s, 1H), 5.65 (s, 1H), 2.52-2.29 (m, 2H), 1.92-1.62 (m, J=6.0 Hz, 8H). Minor isomer: $^1H$ NMR (200 MHz, $CDCl_3$) δ 8.51 (d, J=11.8 Hz, 1H), 6.11 (s, 1H), 2.27-2.09 (m, J=6.4 Hz, 2H), 1.92-1.62 (m, J=6.0 Hz, 8H).

1.2 Synthesis of N-(1-cyanocyclohexyl)-acetamide

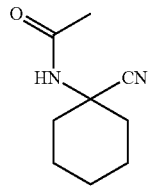

To a stirred solution of aminonitrile (474 mg, 3.62 mmol) and trimethylamine (0.6 mL, 4.28 mmol) in anhydrous $Et_2O$ (6 mL) cooled in an ice bath was added dropwise acetyl chloride (0.3 mL, 4.28 mmol) by syringe. The bath was removed and the reaction was stirred at rt for 3.5 hours. Then, the mixture was filtered through a fritted-glass funnel (medium porosity), and the $Et_2O$ was discarded. Using a second filter flask, the filter cake was washed 4 times with EtOAc. The EtOAc extracts were collected and evaporated to yield 311.7 mg (52% yield) of target compound as a white solid that did not require purification for subsequent reactions. $^1H$ NMR (200 MHz, $CDCl_3$) δ 7.08 (s, 1H), 2.40-2.19 (m, 2H), 1.96 (s, 3H), 1.80-1.40 (m, 8H).

1.3 Synthesis of N-(1-cyano-1-methyl-ethyl)acetamide

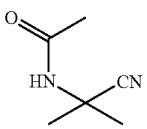

A 100 mL dried two-necked round bottom flask was charged with 2-amino-2-methylpropanenitrile (300 mg, 3.57 mmol) and dissolved in anhydrous EtOAc (14 mL). $K_2CO_3$ (615 mg, 4.44 mmol) was added followed by $Ac_2O$ (0.4 mL, 4.28 mmol). The heterogeneous mixture was stirred for 20 hours at room temperature under argon atmosphere. Then, the crude was filtered and the residue was washed with EtOAc. The resulting solution was concentrated under vacuum. Purified by flash chromatography ($SiO_2$, petroleum ether/EA/Acetone 10:10:1) to yield 150.7 mg (33% yield) of desired product as an off-white solid. $^1H$ NMR (200 MHz, $CDCl_3$) δ 5.78 (s, 1H), 2.01 (s, 3H), 1.70 (s, 6H).

1.4 Synthesis of N-(1-cyano-1-methyl-ethyl)formamide

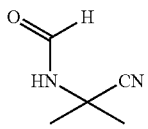

A ca. 20 mL pressure tube (Ace tube) was charged with acetone cyanohydrin (2.55 g, 30.0 mmol), formamide (4.05 g, 90 mmol), and acetic acid (1.7 mL, 30 mmol). The tube was then flushed with argon and closed. It was then placed into a 125° C. pre-heated oil bath and the mixture was stirred at this temperature for 4 h. The reaction was cooled to room temperature. 30 mL of benzene were added and the resulting mixture was concentrated under vacuum and purified without further treatment by flash chromatography (SiO$_2$, CH$_2$Cl$_2$/MeOH 1:0 to 50:1) as an eluent. The product was dried under vacuum to remove residual volatiles and isolated as an yellow oil to yield 1.837 g (91% yield, 9:1 mixture of isomers). $^1$H NMR (200 MHz, CDCl$_3$) δ 8.17 (s, 1H), 6.00 (s, 1H), 1.74 (s, 6H). The signals of the minor isomer are all overlapped with the exception of $^1$H NMR (200 MHz, CDCl$_3$) δ 8.48 (d, J=11.8 Hz, 1H).

1.5 Synthesis of N-(1-cyano-1,2-dimethyl-propyl)formamide

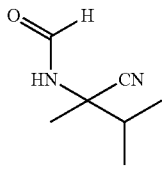

1.5.1 Standard Procedure for the Formyl Protected Aminonitriles of Formula (II)

Freshly prepared acetic-formic anhydride* (1.44 mL, 10 mmol) was added to a stirred solution of the amino-nitrile (2 mmol) in THF (9 mL) at rt under argon atmosphere. The resulting mixture was stirred under these conditions for 65 h. Then, the reaction was treated with aqueous saturated sodium bicarbonate solution (2×30 mL) and subsequently extracted with dichloromethane (3×50 mL). The organic extracts were dried over Na$_2$SO$_4$, evaporated, and the residue was purified by flash column chromatography over silica gel using MeOH/CH$_2$Cl$_2$ (4%) as eluent.

*Acetic-formic anhydride: A MW vial equipped with a stirring bar was charged with 2 mL of Ac$_2$O and 0.88 mL of formic acid, sealed and put under argon. The resulting solution was stirred at 60° C. for 1.5 h. The mixture was cooled down to room temperature and used without further treatment in the subsequent step.

Starting form 2-amino-2,3-dimethylbutyronitrile (224.3 mg, 2 mmol); isolated as a pale-yellow oil (243 mg, 87% yield), as a 3:1 mixture of isomers. Major isomer: $^1$H NMR (200 MHz, CDCl$_3$) δ 8.20 (s, 1H), 5.64 (s, 1H), 2.37 (app dt, J=13.6, 6.8 Hz, 1H), 1.68 (s, 3H), 1.20-1.02 (m, 6H). Minor isomer: $^1$H NMR (200 MHz, CDCl$_3$) δ 8.48 (d, J=11.7 Hz, 1H), 6.13 (s, 1H), 2.00 (app dt, J=14.6, 7.4 Hz, 1H), 1.61 (s, 3H), 1.20-1.02 (m, 6H).

1.6 Synthesis of N-(1-cyano-1-ethyl-propyl)formamide

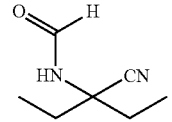

Synthesized following the "Standard procedure for the formyl protected aminonitriles of formula (II) of example 1.5.1.

Starting from 2-amino-2-ethylbutanenitrile (224.3 mg, 2 mmol); isolated as a pale-yellow oil (245 mg, 88% yield), as a 3:1 mixture of isomers. Major isomer: $^1$H NMR (200 MHz, CDCl$_3$) δ 8.19 (s, 1H), 5.73 (s, 1H), 2.06 (app qd, J=7.8, 6.7 Hz, 4H), 1.20-0.99 (m, J=10.8, 7.4 Hz, 6H). Minor Isomer: $^1$H NMR (200 MHz, CDCl$_3$) δ 8.44 (d, J=11.7 Hz, 1H), 6.54 (s, 1H), 1.97-1.76 (m, J=19.4, 10.9, 6.3 Hz, 4H), 1.20-0.99 (m, J=10.8, 7.4 Hz, 6H).

2. Synthesis of Compounds of the Formula (I) by Reductive Hydrolysis of Compounds of the Formula (II)

2.1 Protocol for the reductive nitrile hydrolysis of protected aminonitriles of formula (II)

2.1.1 Synthesis of (1-aminocyclohexyl)methanol

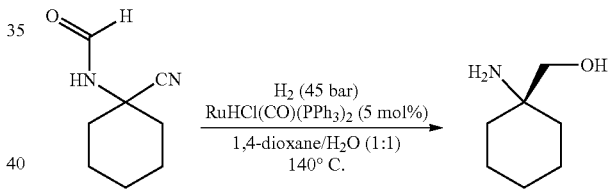

A ca. 40 mL Premex autoclave (equipped with Teflon insert) was charged with RuHCl(CO)(PPh$_3$)$_3$ (47.6 mg, 0.05 mmol), the nitrile (152.2 mg, 1 mmol), 1,4-dioxane (7.0 mL) and H$_2$O (7.0 mL) under air. After closing the reaction vessel, the system was purged first with nitrogen (3×) and then with hydrogen (3×). Finally, the autoclave was pressurized with hydrogen (45 bar) and heated at 140° C. Note: At this temperature the internal pressure rises up to 60 bar. The mixture was stirred under these conditions for 20 h. Then, the reaction was cooled-down on a water bath and depressurized carefully, the organic phase was extracted with EtOAc (3×25 mL), washed with brine and dried over Na$_2$SO$_4$. Filtered through a short cotton pad and concentrated under vacuum. $^1$H-NMR analysis in CDCl$_3$-d showed exclusive formation of deprotected product (>99% conversion). $^1$H NMR (200 MHz, CDCl$_3$) δ 3.32 (s, 1H), 2.09 (br. s, 2H), 1.59-1.31 (m, J=19.1, 11.0 Hz, 8H).

2.2 Evaluation of Conditions for the Preparation of 2-amino-2-methyl-propanol (2-AMP)

2.2.1 Standard Procedure

A ca. 40 mL Premex autoclave (equipped with Teflon insert) was charged with RuHCl(CO)(PPh$_3$)$_3$ (3 mol %), the nitrile 1 (1 mmol) and indicated solvent (7.0 mL) under air. After closing the reaction vessel, the system was purged first with nitrogen (3×) and then with hydrogen (3×). Finally, the autoclave was pressurized with the indicated hydrogen pressure (x bar), and heated at 140° C. The mixture was stirred for the indicated time under the same conditions. Then, the reaction was cooled-down on a water bath and depressurized carefully, the crude mixture was collected in a round bottom flask and concentrated under vacuum. The ratio between the mixtures of products was determined by $^1$H-NMR using MeOD-$d_4$ as solvent.

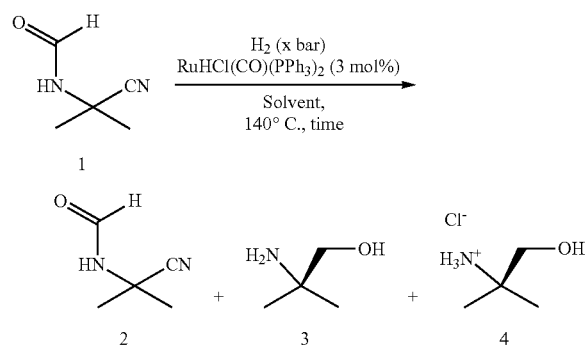

| Solvent | H$_2$ (bar) | Time (h) | Conv (%) | Ratio (2/3/4) | Overall yield (%) |
|---|---|---|---|---|---|
| MeOH | 45 | 18 | >99 | c.m. | — |
| EtOH | 45 | 18 | <5 | traces | — |
| 1,4-dioxane/H$_2$O (6:1) | 45 | 18 | >99 | 2.7/1/— | 89 |
| 1,4-dioxane/H$_2$O (6:1) | 55 | 18 | >99 | 3.5/1/— | 72 |
| 1,4-dioxane/H$_2$O (6:1) | 55 | 65 | >99 | 1/tr/tr | 57 | c.m. = complex mixtures, primary and secondary amines also detected;
tr = traces

2.2.2 Evaluation of Ligands

A ca. 40 mL Premex autoclave (equipped with Teflon insert) was charged with the ruthenium complex (5 mol %) and a corresponding ligand (10 mol %) respectively, the nitrile 1 (1 mmol) and dioxane (7.0 mL) under air. After closing the reaction vessel, the system was purged first with nitrogen (3×) and then with hydrogen (3×). Finally, the autoclave was pressurized with the indicated hydrogen pressure (45-50 bar), and heated at 140° C. The mixture was stirred for 18 h. Then, the reaction was cooled-down on a water bath and depressurized carefully, the crude mixture was collected in a round bottom flask and concentrated under vacuum. The ratio between the mixtures of products was determined by $^1$H-NMR using MeOD-$d_4$ as solvent with hexamethylbenzene as an internal standard.

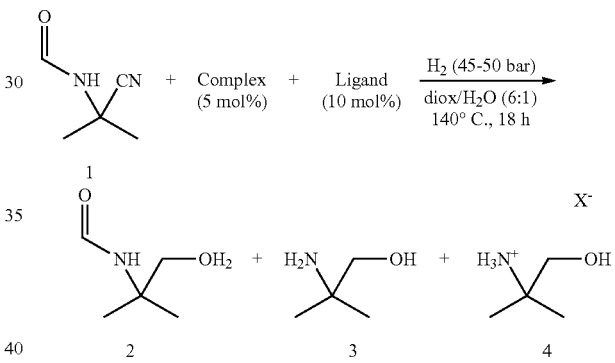

| Complex | Ligand | Conv. (%) | Overall Yield (%) | 2 (%) | 3 (%) | 4 (%) |
|---|---|---|---|---|---|---|
| RuHCOCl(PPh$_3$)$_3$ | Xantphos | 90 | 46 | 46 | <1 | <1 |
| RuHCOCl(PPh$_3$)$_3$ | dppe | <5 | <1 | <1 | <1 | <1 |
| RuHCOCl(PPh$_3$)$_3$ | triphos | >99 | 36 | 29 | 7 | <1 |
| Ru-MACHO ® | — | 85 | 10 | 10 | <1 | <1 |
| Ru-milst-pyridine | — | 46 | 6 | 6 | <1 | <1 |
| Ru-milst-acridine | — | >99 | 24 | 24 | <1 | <1 |

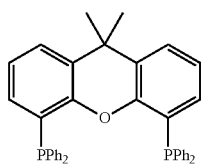

Xantphos

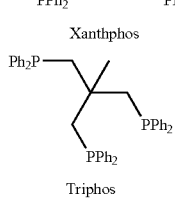

Triphos

| Complex | Ligand | Conv. (%) | Overall Yield (%) | 2 (%) | 3 (%) | 4 (%) |
|---|---|---|---|---|---|---| dppe

Ru-MACHO

Ru-milst-acridine

Ru-milst-acridine

2.2.2.1 Evaluation of Different Metals and Ligands for the Reductive Nitrile Hydrolysis

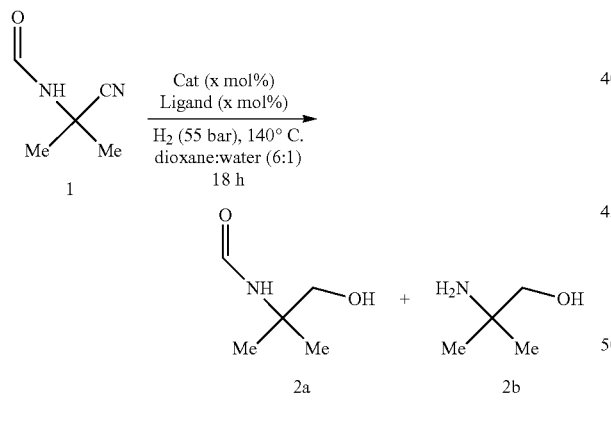

An approximately 40 mL Premex autoclave (equipped with a Teflon insert) was charged with the catalyst, ligand, additive, the protected amino nitrile 1 (0.5 mmol) and solvent. After closing the reaction vessel, the system was purged first with nitrogen (5×) and then with hydrogen (3×). Finally, the autoclave was pressurized with hydrogen (55 bar) and heated at the specified temperature (140° C.). The mixture was then stirred under the same conditions for 18 h. Then, the reaction was cooled-down on a water bath and depressurized carefully. Finally, the crude was analyzed by $^1$H NMR using hexamethylbenzene as internal standard for quantification (0.05 M in $CDCl_3$).

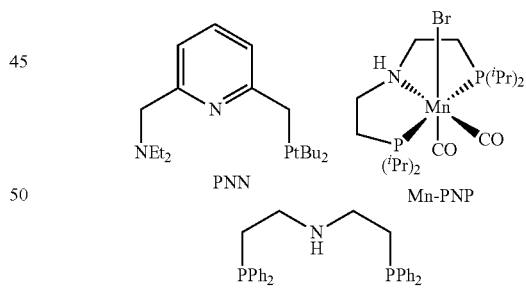

| Entry | Catalyst [mol %] | Additive [mol %] | Base [mol %] | Conversion [%] | NMR Yield [%] 2a | 2b | other |
|---|---|---|---|---|---|---|---|
| RK 1.1-1 | Rh(PPh$_3$)$_3$Cl [5] | — | — | >99 | — | 10 | 14 |
| RK 1.1-2 | [Rh(COD)Cl]$_2$ [5] | Xantphos [10] | — | >99 | — | 24 | 47 (6 species) |

-continued

| Entry | Catalyst [mol %] | Additive [mol %] | Base [mol %] | Conversion [%] | NMR Yield [%] 2a | 2b | other |
|---|---|---|---|---|---|---|---|
| RK 1.1-3 | [Ir(COD)Cl]$_2$ [2.5] | PPh$_3$ [10] | — | 86[a] | — | — | 12 |
| RK 1.1-4 | [Ir(COD)Cl]$_2$ [2.5] | Xantphos [10] | — | 8 | — | — | 8 |
| RK 1.2-1 | Mn-PNP [5] | — | $^t$BuOK [10] | 18 | — | — | — |
| RK 1.2-2 | Co$_2$CO$_8$ [2.5] | PPh$_3$ [10] | — | 38 | — | — | 31 |
| RK 1.2-3 | CoCl$_2$ [5] | PNN [10] | NaOEt [10] | 23 | — | — | 22 |
| RK 1.2-4 | CoCl$_2$ [5] | PPh$_3$ [10] | — | 41 | — | — | ? |
| RK 1.2-5 | CoCl$_2$ [5] | Xantphos [10] | — | 23 | — | — | — |
| RK 1.2-6 | CoCl$_2$ [5] | P$^{Ph}$NP$^{Ph}$ [6] | NaOEt [20] | 21 | — | — | — |
| RK 1.2-7 | — | — | NaOEt [20] | 20 | — | — | — |
| RK blank | — | — | — | <1 | — | — | — |

[a]Conversion after aqueous work-up

2.2.3 Evaluation of Pressure Effect

For experiments under higher pressure, a 160 ML stainless steel autoclave without teflon lining, equipped with a magnetically coupled overhead stirrer with inclined blades, electrical heating mantle and H2-inlet was used. A solution of 0.6 g (0.005 mol) nitrile 1 in 25.7 g dioxane and 4.3 g water was put into the autoclave beaker, 0.153 g of RuHCl (CO)(PPh$_3$)$_3$ (3 mol %) were added, the autoclave was closed and flushed with argon. Then, the autoclave was pressurized at room temperature to 20 bar with hydrogen and with stirring, the autoclave was heated to 150° C. The pressure was adjusted to 55 bar at this temperature by charging hydrogen to the autoclave and the mixture was stirred for 24 h. After this time, it was allowed to cool to room temperature and depressurized. A sample was taken and analyzed as described below (sample 1). After this, the autoclave was pressurized to 20 bar again, heated to 150° C. and the pressure increased to 135 bar. The mixture was stirred under these conditions for another 24 h after which a further sample was taken in a similar way as before (sample 2).

The samples were analyzed by gas chromatography using a column of type RTX5 Amine, length 30 m, with diameter 0.32 mm and layer thickness 1.5 μm, FID detector. Temperature program: injection at 60° C., heating up with 4° C./min to 280° C., holding 15 minutes at 280° C. Results given in area percent, solvent signal was excluded and water was not detected.

| Sample | 2-AMP | Nitrile 1 | N-formyl-2-AMP |
|---|---|---|---|
| 1 | 58.3 | 3.9 | 22.0 |
| 2 | 74.3 | 1.5 | 7.8 |

The purity by GC of the starting nitrile 1 was 84% (area-%). Thus, a maximum of about 84% of desired product peak area would be expected, which compares well with the amount found (74.3% of 2-AMP). The calculated selectivity based on the initial peak area of 84% for starting material would amount to 89% for sample 2. Sample 2 was also analyzed using an internal standard (diglyme) in order to quantify the mass of product formed. The crude product solution was found to contain 1.16 mass-% of 2-AMP, which corresponds to a molar yield of 73% of product 2-AMP, and 0.16% of N-formyl-2-AMP which corresponds to a molar yield of 8% of N-formyl-2-AMP.

Thus, it was shown that higher pressure favorizes the deprotection of the amino group as the ratio of 3 to 2 was far higher than that achieved before at higher yield (about 9.5:1 at a combined yield of 81%).

In the same set-up and according to the same procedure, the triphos and xantphos ligands were also tested using 3 mol-% of catalyst (RuHCl(CO)(PPh$_3$)$_3$/ligand 1:1) at two different pressure levels. The experiments were run at 140° C. for 24 h. The purity of the starting nitrile (95% with triphos and 91% with xantphos) was accounted for in the calculation of the yield.

Triphos:

| Sample | 2-AMP | Nitrile X | N-formyl-2-AMP | Molar yield 2-AMP | Molar yield N-formyl-2-AMP |
|---|---|---|---|---|---|
| 1 | 41.0 | 0.74 | 33.7 | 45.9 | 28.6 |
| 2 | 71.6 | 0 | 13.0 | 69.8 | 16.0 |

Xantphos

| Sample | 2-AMP | Nitrile X | N-formyl-2-AMP | Molar yield 2-AMP | Molar yield N-formyl-2-AMP |
|---|---|---|---|---|---|
| 1 | 55.8 | 0 | 15.50 | 48.9 | 10.3 |
| 2 | 61.3 | 0 | 4.2 | 57.2 | 3.0 |

Thus, it was shown again that higher pressure favorizes the deprotection of the amino group also in the case of multidentate ligands as the ratio of 3 to 2 was far higher than that achieved before at higher yield (about 5.5:1 at a combined yield of 85% for triphos and 14.6:1 at a combined yield of 60% for xantphos).

2.2.4 Evaluation of Salt Effect

Standard procedure: A ca. 40 mL Premex autoclave (equipped with Teflon insert) was charged with indicated additive (1 equiv.), RuHCl(CO)(PPh$_3$)$_3$ (X mol %), the nitrile 1 (1 mmol), dioxane (6.0 mL) and H$_2$O (1.0 mL) under air. After closing the reaction vessel, the system was purged first with nitrogen (3×) and then with hydrogen (3×). Finally, the autoclave was pressurized with hydrogen (55 bar), and heated at 140° C. Note: At this temperature the internal pressure rises up to 70 bar. The mixture was stirred for 17 h. Then, the reaction was cooled-down on a water bath and depressurized carefully, the crude mixture was collected in a round bottom flask and concentrated under vacuum. 0.3 mmol of hexamethylcyclotrisiloxane or 1 mmol of Cl$_2$CH$_2$CH$_2$Cl$_2$ (used as internal standard) were added to the crude mixture to determine the $^1$H-NMR yield in MeOD-d$_4$.

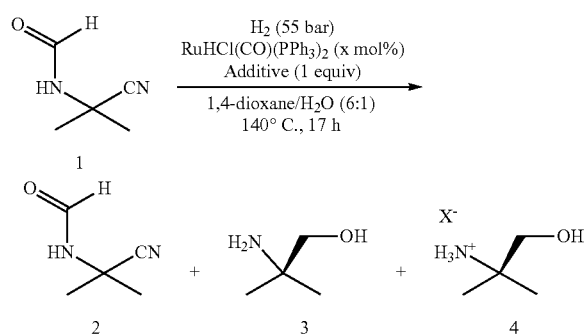

| mol % [Ru] | Additive | Conv (%) | 2 (yield, %) | 3 (yield, %) | 4 (yield, %) |
|---|---|---|---|---|---|
| 2 | — | 90 | 86 | 3 | — |
| 2 | NaCl | 83 | 26 | — | 57 |
| 3 | (NH$_4$)$_2$SO$_4$ | >99 | 53 | — | 30 |
| 3 | Na$_2$SO$_4$ | >99 | 50 | 28 | — |
| 3 | (NH$_4$)H$_2$PO$_4$ | >99 | 60 | — | 29 |
| 3 | Yb(OTf)$_3$* | <75% | 70 | — | — |

*In this case, only 5 mol % of additive was used.

$^1$H NMR (200 MHz, MeOD) δ 3.28 (s, 2H), 1.06 (s, 6H).

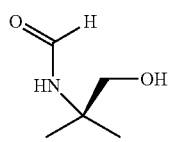

Isolated as a 2.5:1 mixture of isomers: Major isomer: $^1$H NMR (200 MHz, MeOD) δ 7.92 (s, 1H), 3.58 (s, 2H), 1.30 (d, J=0.6 Hz, 6H). Minor isomer: $^1$H NMR (200 MHz, MeOD) δ 8.21 (s, 1H), 3.39 (s, 2H), 1.27 (d, J=0.7 Hz, 6H).

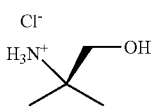

$^1$H NMR (200 MHz, MeOD) δ 3.48 (s, 1H), 1.29 (s, 1H).

2.2.5 Isolation as an HCl Adduct

Method A)

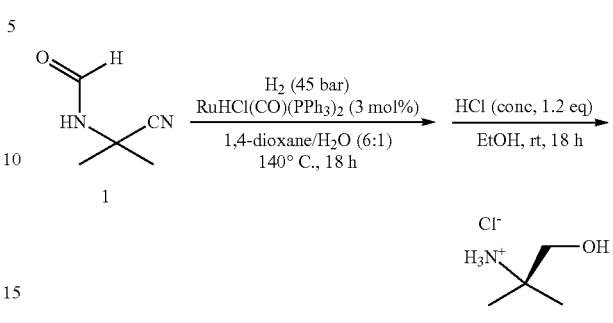

A ca. 40 mL Premex autoclave (equipped with Teflon insert) was charged with RuHCl(CO)(PPh$_3$)$_3$ (3 mol %), the nitrile 1 (1 mmol), dioxane (6.0 mL) and H$_2$O (1.0 mL) under air. After closing the reaction vessel, the system was purged first with nitrogen (3×) and then with hydrogen (3×). Finally, the autoclave was pressurized with hydrogen (45 bar) and heated at 140° C. Note: At this temperature the internal pressure rises up to 60 bar. The mixture was stirred for 18 h. Then, the reaction was cooled-down on a water bath and depressurized carefully, the crude mixture was collected in a round bottom flask and concentrated under vacuum. Subsequently, it was dissolved in 1 mL of EtOH. 0.1 mL of concentrated HCl (36%) were added to the solution. The resulting mixture was stirred at room temperature for 18 hours. Then, the mixture was concentrated under reduced pressure and it was washed with Et$_2$O (×3) and dried under vacuum. The product was isolated as an off-white solid (67.1 mg, 54% yield over two steps). $^1$H NMR (200 MHz, D$_2$O) δ 3.55 (s, 2H), 1.31 (s, 6H).

Method B)

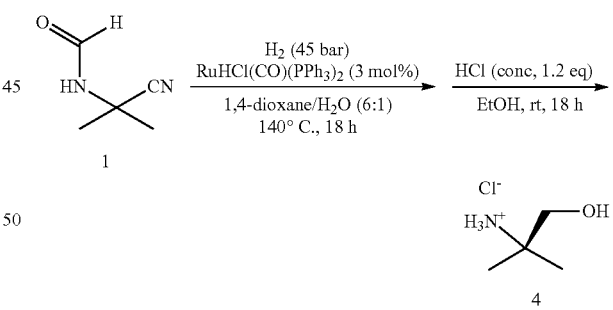

A ca. 40 mL Premex autoclave (equipped with Teflon insert) was charged with RuHCl(CO)(PPh$_3$)$_3$ (3 mol %), the nitrile 1 (1 mmol), dioxane (6.0 mL) and H$_2$O (1.0 mL) under air. After closing the reaction vessel, the system was purged first with nitrogen (3×) and then with hydrogen (3×). Finally, the autoclave was pressurized with hydrogen (55 bar) and heated at 140° C. Note: At this temperature the internal pressure rises up to 60 bar. The mixture was stirred for 18 h. Then, the reaction was cooled-down on a water bath and depressurized carefully, the crude mixture was collected in a round bottom flask and concentrated under vacuum. Subsequently, it was dissolved in 2.5 mL of MeOH. To the solution, 2.5 mL of a 2 M HCl aqueous solution were added. The mixture was stirred at 80° C. for 18 hours. Then, the mixture was concentrated under reduced pressure and it was washed with Et$_2$O (×3) and dried under vacuum. The product was isolated as an off-white solid (74.2 mg, 59% yield over two steps). $^1$H NMR (200 MHz, D$_2$O) δ 3.55 (s, 2H), 1.31 (s, 6H).

2.2.6 Isolation as an HCl Adduct, Substrate Scope

The corresponding formyl-protected aminonitriles were prepared according to the procedures 1.3 or 1.4, 1.51. The reactions on the substrate scope were performed as followed: A ca. 40 mL Premex autoclave (equipped with Teflon insert) was charged with RuHCl(CO)(PPh$_3$)$_3$ (5 mol %), the formyl protected aminonitrile (1 mmol), dioxane (6.0 mL) and H$_2$O (1.0 mL) under air. After closing the reaction vessel, the system was purged first with nitrogen (3×) and then with hydrogen (3×). Finally, the autoclave was pressurized with hydrogen (55 bar) and heated at 140° C. Note: At this temperature the internal pressure rises up to 60 bar. The mixture was stirred for 18 h. Then, the reaction was cooled-down on a water bath and depressurized carefully, the crude mixture was collected in a round bottom flask and concentrated under vacuum. Subsequently, it was dissolved in 2.5 mL of MeOH. To the solution, 2.5 mL of a 2 M HCl aqueous solution were added. The mixture was stirred at 80° C. for 18 hours. Then, the mixture was concentrated under reduced pressure and it was washed with Et$_2$O (×3) and dried under vacuum to obtain the corresponding amino alcohols in the form of their HCl-salts.

The product yields were determined by $^1$H-NMR spectroscopy in CDCl$_3$.

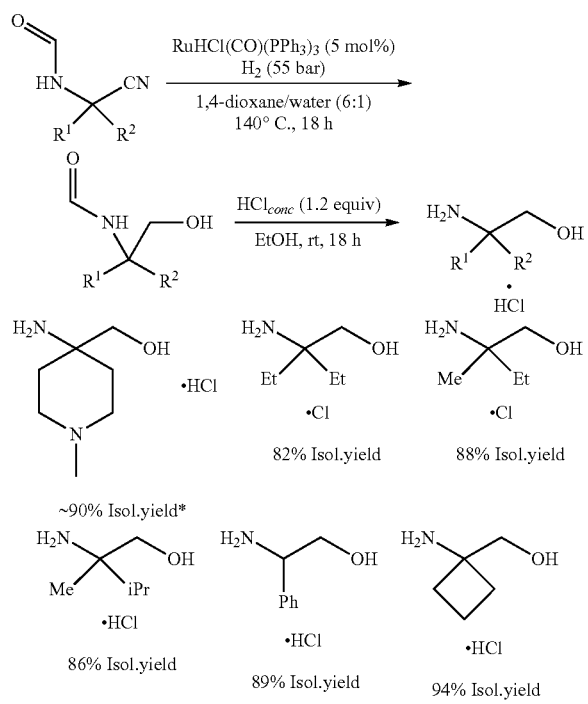

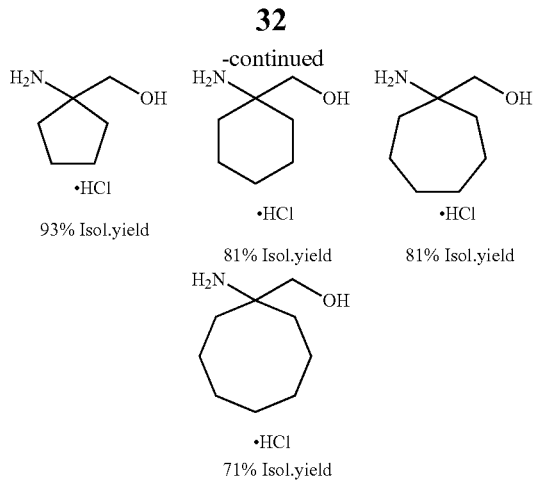

2.2.3 Comparative Examples

Stability of non-protected aminonitriles at elevated temperatures in the presence of water: 2-amino-2-methyl-propanenitrile was dissolved in D$_2$O/MeOH-d$_4$ (1:1) in an J-young NMR-tube and heated for 2 hours at 140° C. The reaction mixture was analyzed by $^1$H-NMR. It was detected, that the aminonitrile is hydrolyzed to the ketone, HCN and NH$_3$, which showed that unprotected aminonitriles are not stable under the conditions required for the reductive nitrile hydrolysis. Therefore the amine function has to be protected.

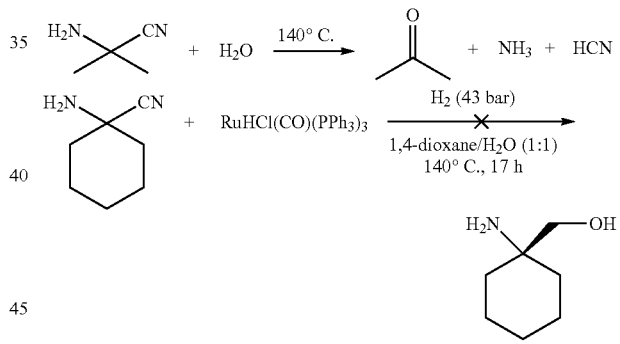

A ca. 40 mL Premex autoclave (equipped with Teflon insert) was charged with RuHCl(CO)(PPh$_3$)$_3$(48.1 mg, 0.05 mmol), 1-aminocyclohexane-1-carbonitrile (124.2 mg, 1 mmol), 1,4-dioxane (7.0 mL) and H$_2$O (7.0 mL) under air. The mixture was degassed gently with argon. After closing the reaction vessel, the system was purged first with nitrogen (3×) and then with hydrogen (3×). Finally, the autoclave was pressurized with hydrogen (43 bar) and heated at 140° C. Note: At this temperature the internal pressure rises up to 60 bar. The mixture was stirred under these conditions for 17.5 h. Then, the reaction was cooled-down on a water bath and depressurized carefully, the organic phase was extracted with EtOAc (3×25 mL), washed with brine and dried over Na$_2$SO$_4$. Filtered through a short cotton pad and concentrated under vacuum. $^1$H-NMR analysis in CDCl$_3$-d showed no formation of expected product.

Thus, this experiment suggests that the reductive hydrolysis of nitrile group occurs faster than the deprotection of formyl amino group.

The invention claimed is:

1. A process for producing a compound of the formula (I)

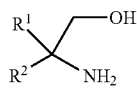 (I)

wherein in the formula (I)
R¹ is hydrogen or an organic radical having from 1 to 40 carbon atoms,
R² is an organic radical having from 1 to 40 carbon atoms,
or R¹ and R² together with the atoms connecting them, form a divalent organic group having from 1 to 40 carbon atoms,
the process comprising:
reacting a compound of the formula (II)

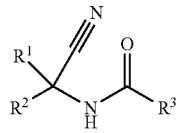 (II)

wherein in the formula (II)
R¹ and R² have the same meaning as in formula (I), and
R³ is hydrogen or an organic radical having from 1 to 40 carbon atoms,
with hydrogen and water in the presence of an ether solvent and at least one homogeneous transition metal catalyst (TMC 1) selected from [Ru(PPh$_3$)$_3$(CO)(H)Cl],
in a molar ratio of water to ether solvent of 2:1 to 1:50.

2. The process according to claim 1, wherein R³ is hydrogen.

3. The process according to claim 1, wherein the at least one homogeneous TMC 1 is [Ru(PPh$_3$)$_3$(CO)(H)Cl] in combination with 1,1,1-tris(diphenylphosphinomethyl)ethane (Triphos) or bis(diphenylphosphino)-9,9-dimethylxanthene (Xantphos).

4. The process according to claim 1, wherein the at least one homogeneous TMC 1 is used in an amount of 0.001 mol % to 20 mol %, calculated as transition metal and based on the amount of the compound of the formula (II) used in the process.

5. The process according to claim 1, wherein the reaction between the compound of the formula (II), water, and hydrogen is performed at a pressure in the range from 10 to 180 bar.

6. The process according to claim 1, wherein the reaction between the compound of the formula (II), water, and hydrogen is performed at a temperature in the range from 50° C. to 180° C.

7. The process according to claim 1, wherein the at least one homogeneous TMC 1 is recycled by removing the compound of the formula (II) and other volatile compounds of a reaction mixture obtained after the reaction between the compound of the formula (II), water, and hydrogen, via distillation.

8. The process according to claim 1, wherein the reaction between the compound of the formula (II), water, and hydrogen is carried out at different H$_2$ pressures,
wherein a lower H$_2$ pressure in the range from 1 to 80 bar is used at first to reduce the nitrile group of the compound of the formula (II), and afterwards H$_2$ pressure is increased to a pressure in the range from 90 to 200 bar to reduce the amide group of the compound of the formula (II).

* * * * *